United States Patent [19]

Haber et al.

[11] Patent Number: 5,336,186
[45] Date of Patent: Aug. 9, 1994

[54] SAFETY SYRINGE WITH DISPLACEABLE BARREL HUB

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 16,817

[22] Filed: Feb. 10, 1993

[51] Int. Cl.5 .............................................. A61M 5/00
[52] U.S. Cl. ..................................... 604/110; 604/195
[58] Field of Search ............... 604/110, 187, 198, 195, 604/263

[56] References Cited

U.S. PATENT DOCUMENTS

| | | |
|---|---|---|
| 4,026,287 | 5/1977 | Haller . |
| 4,507,117 | 3/1985 | Vining et al. . |
| 4,808,169 | 2/1989 | Haber et al. . |
| 4,834,717 | 5/1989 | Haber et al. . |
| 5,030,208 | 7/1991 | Novacek et al. ............... 604/195 |
| 5,098,402 | 3/1992 | Davis ................................. 604/110 |
| 5,112,316 | 5/1992 | Venturini ......................... 604/195 |

Primary Examiner—John D. Yasko
Attorney, Agent, or Firm—Townsend & Townsend Khourie & Crew

[57] ABSTRACT

A safety syringe (2) includes a hollow barrel (4) with a barrel hub (24) threadably mounted to and dismountable from the distal end (4) of the barrel. A plunger (10) has a piston (14) at its distal end (20). The plunger and the barrel hub are configured to permit the distal end of the plunger to engage the barrel hub at the conclusion of an injection, typically through a splined interface (46, 52), to allow positive rotary engagement of the barrel hub by the plunger. Thereafter, the plunger is used to withdraw the barrel hub and needle (43) back into the interior (23) of the barrel. The plunger can be fractured at a weakened region (57) adjacent the piston thus leaving the distal end of the plunger, piston, barrel hub and needle housed within the barrel interior. The hollow stem can then be inserted through the distal end of the barrel and over the needle for compact disposal.

9 Claims, 6 Drawing Sheets

SAFETY SYRINGE WITH DISPLACEABLE BARREL HUB

CROSS-REFERENCE TO RELATED APPLICATION

This application is related to and is an improvement over the syringe disclosed in U.S. Pat. No. 4,710,170, the disclosure of which is incorporated by reference.

BACKGROUND OF THE INVENTION

Hypodermic syringes, once contaminated, can be a source of dangerous and sometime fatal infectious diseases. Contaminated hypodermic needles, if not properly handled after use, can result in an unintentional needle stick of a health care worker. In addition, illicit use of used syringes can occur if the syringes are not properly disabled after use.

In response to some of these problems, a disposable, anti-needle-strike, anti-drug abuse syringe was developed and is disclosed in U.S. Pat. No. 4,170,170. The plunger on this syringe has a tapered opening which is used to engage a similarly tapered extension of the needle hub at the distal end of the barrel. This provides a frictional engagement which permits the user to rotate the needle hub, thus disconnecting it from the distal end of the barrel, by rotating the stem of the plunger. The frictional interface between the tapered opening and the tapered extension is designed to be sufficient to enable the user to pull the coupled needle assembly from the distal end of the barrel into the interior of the barrel shown in FIG. 14 in the patent. At this point the stem, which has a weakened region adjacent the piston, is snapped into two pieces leaving the distal end of the stem, the piston and the needle assembly inside the interior of the barrel. The hollow stem can then be inserted through the now open distal end of the barrel to cover the needle assembly and to permit compact disposal.

While this safety syringe provides significant advantages over existing safety syringes, the smooth, frustoconically shaped friction drive surfaces, being surfaces of revolution with respect to the syringe axis, proved less than ideal. One of the problems was the manufacturing tolerances for a good frictional fit between the frustoconical surfaces were quite close. Also, if moisture contaminated the tapered surfaces, especially if there was not good alignment between the two parts, the frictional engagement might not be sufficient to either disengage the barrel hub from the barrel or pull the barrel hub back into the barrel.

SUMMARY OF THE INVENTION

The present invention is directed to a safety syringe which is simple in construction and yet provides a positive rotary drive interface between the plunger and the barrel hub to ensure proper disengagement of the barrel hub from the barrel while eliminating sensitive tolerance and alignment aspects of a known safety syringe.

The safety syringe, of the type in which the needle assembly is shielded after use, includes a hollow barrel with a barrel hub threadably mounted to and dismountable from the distal end of the barrel. A plunger has a piston at its distal end. The plunger and the barrel hub are configured to permit the distal end of the plunger to engage the barrel hub at the conclusion of an injection; the engagement is typically through a serrated or splined interface or other interfaces which do not rely totally on surface friction to allow the positive rotatable engagement of the barrel hub by the plunger. The rotary drive, the barrel hub and plunger are also configured to permit the plunger to withdraw the barrel hub and needle assembly mounted thereto back into the interior of the barrel after the barrel hub has been detached from, typically unscrewed from, the distal end of the barrel. At this point the plunger, which preferably has a weakened region adjacent the piston, can be fractured at the weakened region thus leaving the distal end of the plunger, the piston, the barrel hub and the needle housed within the interior of the barrel. The stem, which is preferably hollow, can then be inserted through the distal end of the barrel and over the needle assembly for compact disposal.

The barrel hub is preferably threadably mounted to the distal end of the barrel. This, coupled with a tapered interface between the barrel hub and the interior surface of the barrel, permits a secure fluid-tight seal between the two components without requiring tolerances as tight as would be required if, for example, a bayonet or twist-lock type of securement were used. Due to the positive rotary drive interface between the plunger and the barrel hub, there is no problem with exerting sufficient torque to unscrew the barrel hub from the barrel.

Other features and advantages of the invention will appear from the following description in which the preferred embodiment has been set forth in detail in conjunction with the accompanying drawings.

DESCRIPTION OF THE PREFERRED EMBODIMENT

Figure 1:
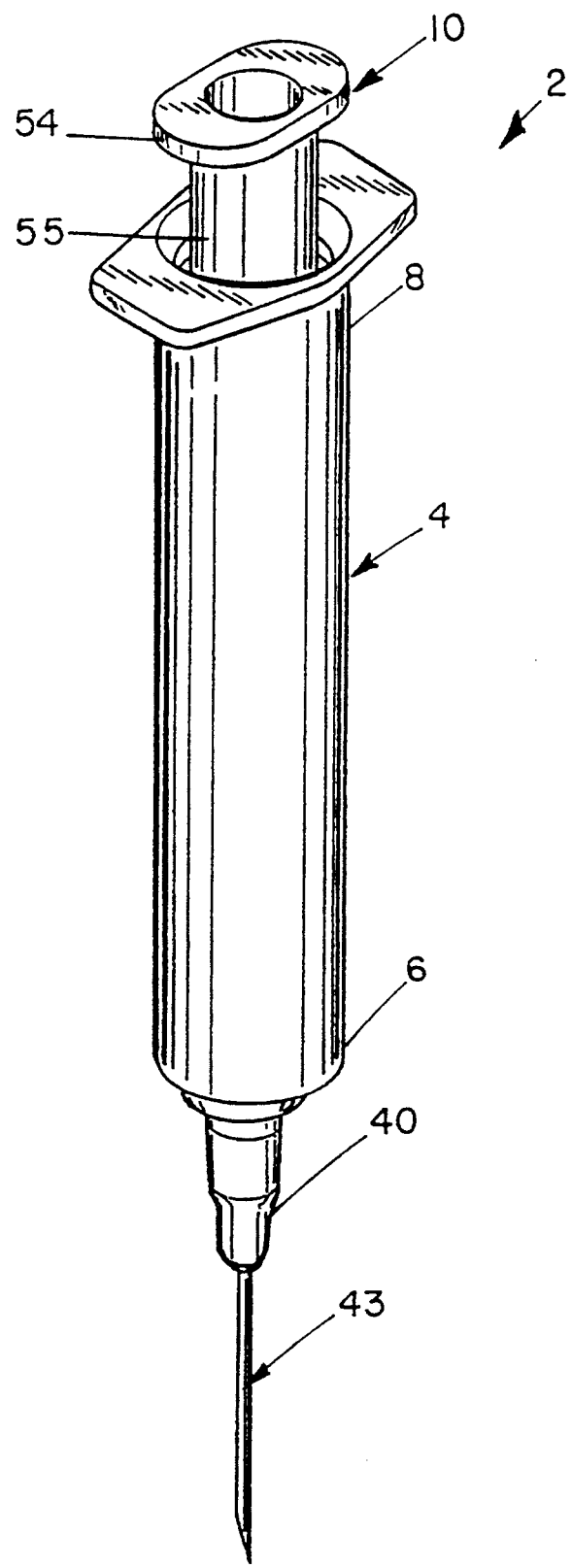
FIG. 1 is an isometric view of a safety syringe made according to the invention in its pre-use condition.
Figure 2:
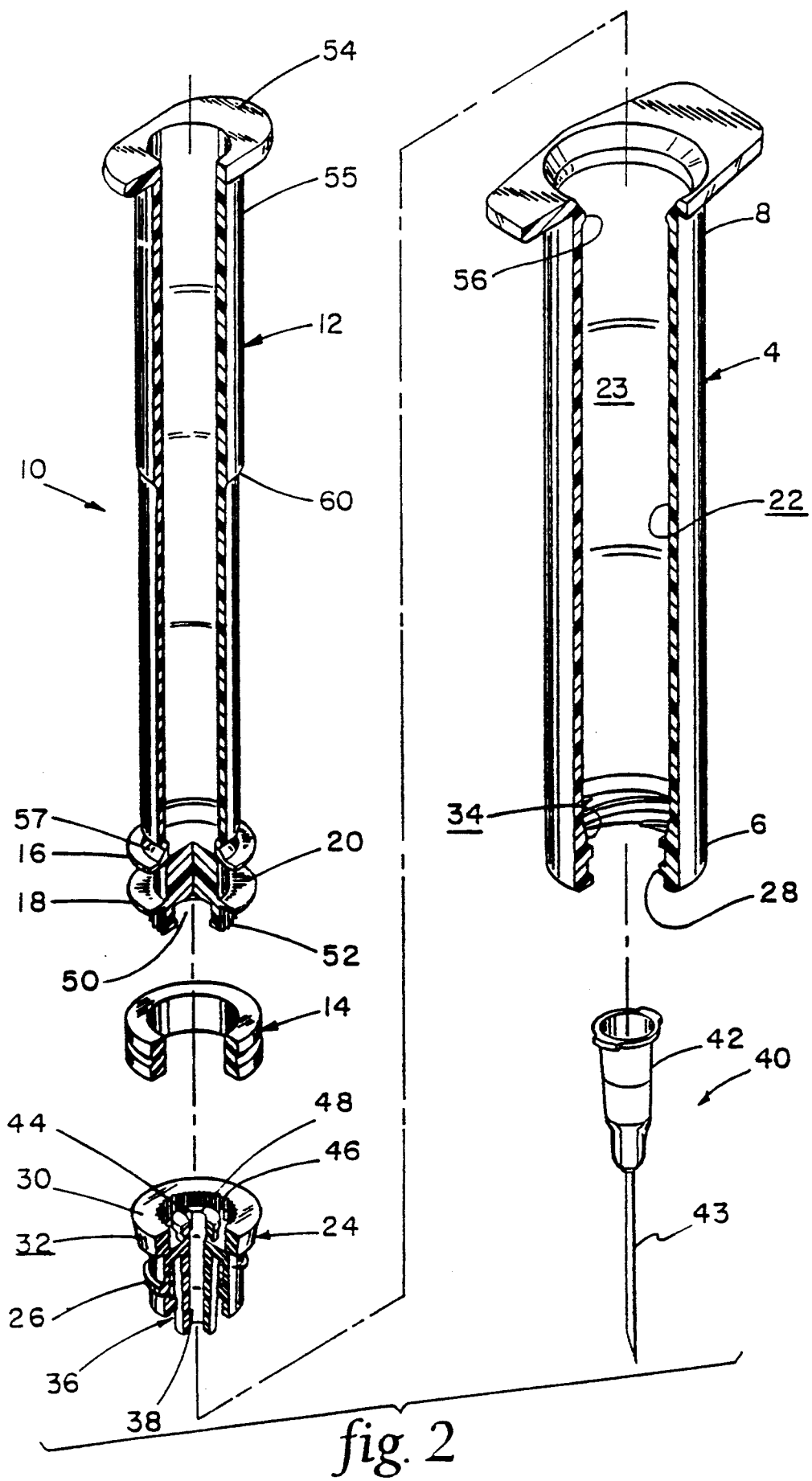
FIG. 2 is an exploded isometric view of the syringe of FIG. 1.

FIGS. 1 and 2 illustrate a safety syringe 2 including a barrel 4 having a distal end 6 and a proximal end 8. Syringe 2 also includes a plunger 10 made of an elongate stem 12 and a seal ring 14. Seal ring 14 is mounted between a pair of flanges 16, 18 at the distal end 20 of stem 12. Seal ring 14 is sized to engage the inner surface 22 defining the interior 23 of barrel 4 so that the distal end 20 of stem 12 acts as a piston.

Syringe 2 also includes a barrel hub 24 having external barrel threads 26 formed at a distal end thereof and sized to engage internal barrel threads 28 formed at distal end 6 of barrel 4. Barrel hub 24 also has a tapered flange 30 at its proximal end with an externally facing tapered surface 32. Tapered surface 32 is sized and positioned to engage a complementary tapered surface 34 formed within barrel 4 adjacent internal threads 28. In this way, barrel hub 24 can be screwed tightly onto distal end 6 of barrel 4, using threads 26, 28, to provide a good fluid seal between hub 24 and barrel 4 through the engagement of mating surfaces 32, 34.

Barrel hub 24 has a conventional Luer lock fitting 36 surrounding a central fluid bore 38. Luer lock fitting 36 is sized to engage a conventional needle assembly 40 of the type having a needle hub 42 and hollow needle canula 43.

Barrel hub 24 has an annular opening 44 defined by internal splines 46 around its circumference and a bulbous, segmented plug 48 at its center. Segmented plug 48 is sized to snap fit within a pocket 50 formed at distal end 20 of stem 12. The part of distal end 20 surrounding pocket 50 has external splines 52 formed thereon. Splines 46, 52 are sized for complementary mating engagement when segment plug 48 snapped into pocket 50 as discussed below.

Figure 1A:
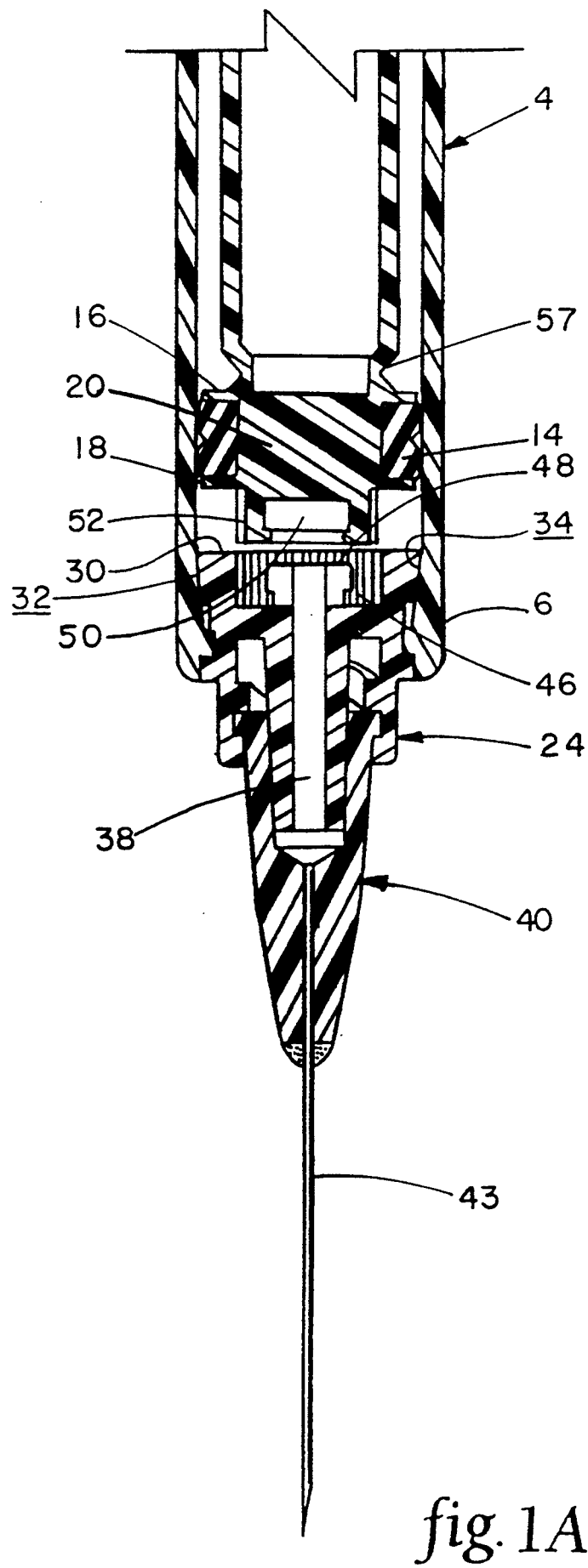
FIG. 1A is cross-sectional view of the distal portion of the syringe of FIG. 1.
Figure 3:
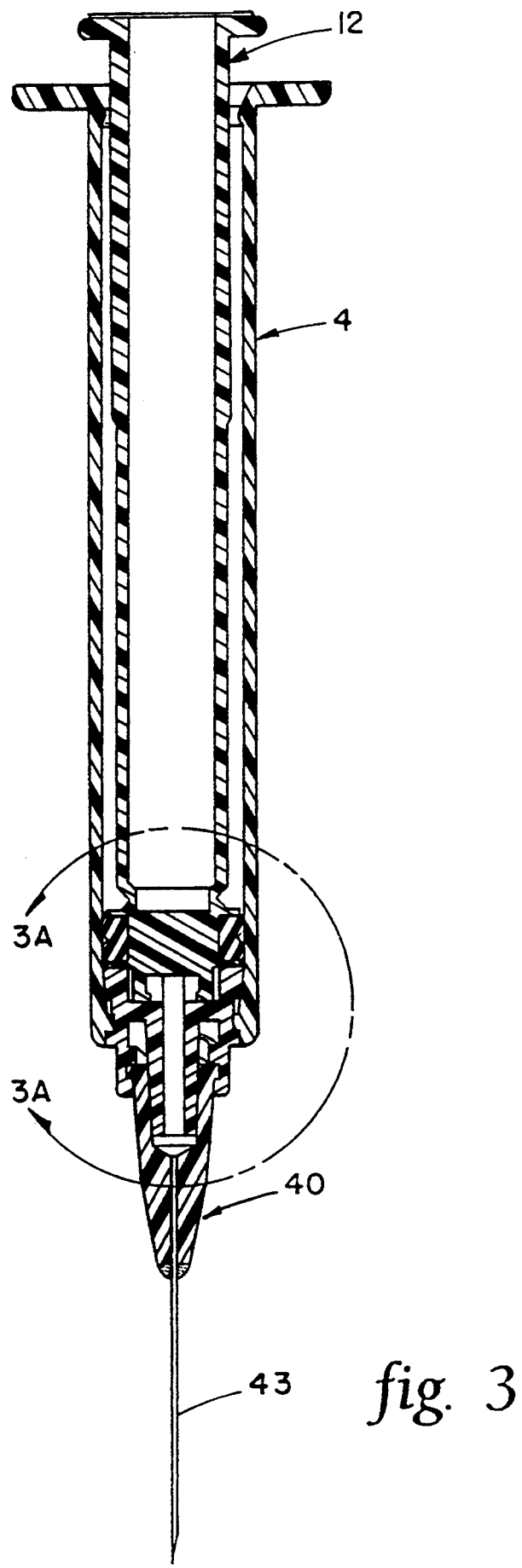
FIG. 3 is a cross-sectional view of the safety syringe of FIG. 1 in the post-injection position.
Figure 3A:
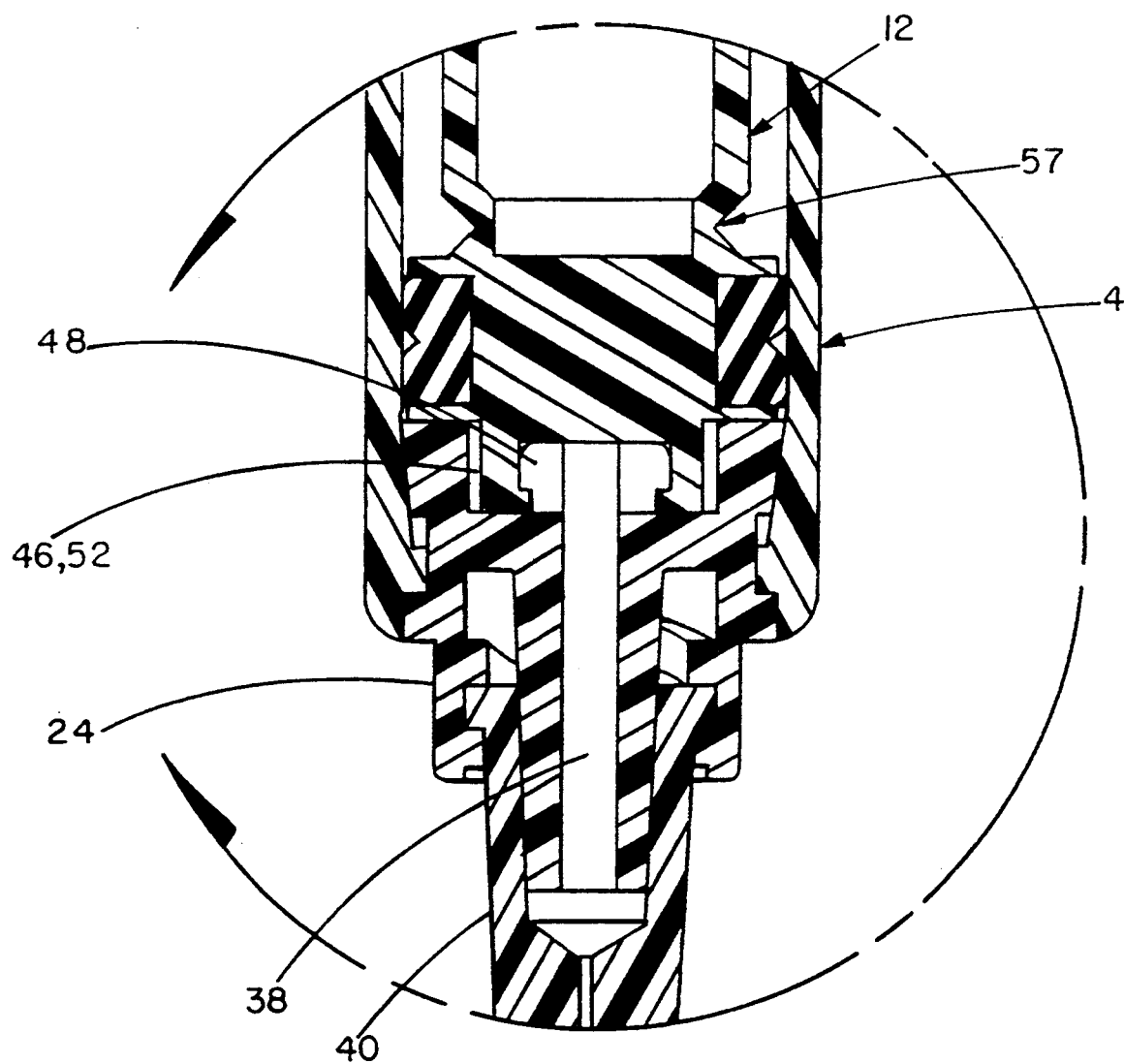
FIG. 3A is an enlarged view taken along line 3A—3A of FIG. 3.
Figure 4:
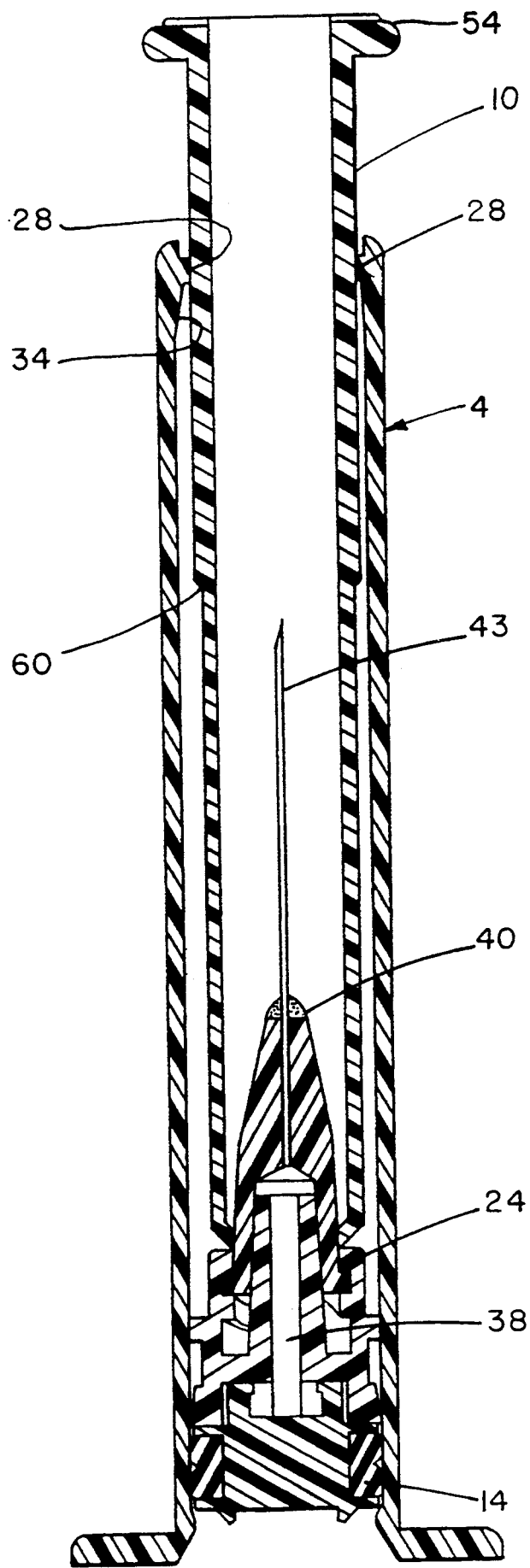
FIG. 4 is an enlarged cross-sectional view of the syringe of FIG. 1 shown after use in a safe/disposal condition.

FIGS. 1 and 1A illustrate syringe 2 in its pre-use condition. As can be seen in FIG. 1A, plunger 10 and barrel hub 24 are not engaged. The user then fills syringe 2 in a conventional manner and gives the injection. FIGS. 3 and 3A illustrate syringe 2 in its post-injection condition with plunger 10 having been driven against barrel hub 24 so that segmented plug 48 enters pocket 50 and splines 46, 52 engage. This permits the user to uncouple barrel hub 24 from barrel 14 by grasping the oblong stem flange 54 at the proximal end 55 of stem 12 and rotating stem 12 relative to barrel 4. The positive engagement created by splines 46, 52 permit a great deal of torque to be applied to barrel hub 24 allowing the user to easily overcome the frictional engagement between threads 26, 28. After unscrewing barrel hub 24 from distal end 6 of barrel 4, barrel hub 24 and needle assembly 40 therewith are pulled into interior 23 of barrel 4 to the position shown in FIG. 4 by pulling plunger 10 proximally relative to barrel 4. This proximal motion is possible due to the engagement of plug 48 within pocket 50. The proximal motion is halted by the engagement of tapered flange 30 of barrel hub 24 with an internal flange 56 at proximal end 8 of barrel 4. At this point, the user can break apart stem 12 adjacent proximal flange 16 by pushing stem 12 laterally, causing stem 12 to break at a weakened region 57 adjacent flange 16. While someone could push the assembly of distal end 20 of stem 12, sealing ring 14, barrel hub 24, and needle assembly 40 back down barrel 4, the syringe is no longer functional because distal end 20 of stem 12 cannot be separated from barrel hub 24 and the severed portion 58 of the stem cannot be reattached to hub 24.

For additional safety and reduced debris bulk, the separated stem portion 58 can be inserted through distal end 6 of barrel 4 until the severed portion covers needle assembly 40. To help retain stem portion 58 within barrel 4, stem 12 has a step 60 along its length so that the outside diameter of stem 12 is larger at proximal end 55 of stem 12 than on the other side of step 60. This enlarged diameter frictionally engages internal threads 28 to help keep severed portion 58 in place.

In use, syringe 2, in its pre-use condition of FIGS. 1 and 1A, is filled with a pharmaceutical in a conventional fashion by inserting hollow needle cannula 43 into a vial or other pharmaceutical container. The user then grasps stem flange 54 and pulls plunger 10 in a proximal direction, thus aspirating the liquid pharmaceutical into interior 23 of barrel 4. The injection is given in a conventional manner by pushing plunger 10 back into barrel 4. After the injection has been given, plunger 10 is driven distally until it assumes the position of FIGS. 3 and 3A. At this point, the user can unscrew barrel hub 24 from distal end 6 of barrel 4 by rotating plunger 10 relative to barrel 4 through the positive engagement of splines 46, 52. After being unthreaded, plunger 10 is pulled proximally, thus pulling barrel hub 24 and needle assembly 40 into interior 23 of barrel 4. Once in the position of FIG. 4, severed portion of stem 12 is snapped off from the remaining portion of the stem at weakened region 57 adjacent flange 16 to permanently disable the syringe. Portion 58 is then inserted through distal end 6 of barrel 4 and over needle assembly 40 for disposal.

Other types of rotatable locking structures can be used to mount barrel hub 24 to distal end 6 of barrel 4. The threaded mounting arrangement is, however, preferred because of the high force it can create between tapered surfaces 32, 34 without the need for tight tolerances, as are often required when a bayonet-type of rotary lock mechanism is used.

The components used in syringe 2 are of pharmaceutically compatible materials. For example, seal ring 14 is preferably a medical grade silicone rubber while hollow needle 43 is stainless steel. The remaining components are made of medical grade plastic, such as polycarbonate, or other suitable materials. The choice of these materials for the preferred embodiment does not, of course, limit the use of other suitable materials as well.

Further modifications and variation can be made to the disclosed embodiment without departing from the subject of the invention as defined in the following claims. For example, instead of the use of splines 46, 52 and segmented plug 48/pocket 50, plunger 10 and barrel hub 24 could be secured to one another using other connecting structures in which abutting, interfering rotary drive surfaces provide positive rotational engagement as opposed to the purely sliding frictional engaging provided by the syringe disclosed in the above-mentioned patent. For example, a bayonet or twist lock type of connecting structure could be used to provide both the rotational and axial movement interfaces needed. Also, severed portion 58 of stem 12 could be more positively locked within barrel 4 than through the use of frictional engagement. For example, severed portion 58 could include threads to engage internal threads 28. Also, some type of locking ledges or fingers could be incorporated into the outer surface of stem 12 near proximal end 55 to prevent removal of severed portion 58 of stem 12 from barrel 4 when in the safe/disposal condition of FIG. 4. Similarly, locking ledges or fingers could also be used to positively engage hub 24 when in the position of FIG. 4.

What is claimed is:

1. A safety syringe comprising:
   a barrel having proximal and distal ends and a hollow interior defining an axis;
   a barrel hub threadably mountable to and dismountable from the distal end of the barrel;
   a plunge, having proximal and distal ends, including a piston at the distal end of the plunger, the piston movable within the hollow interior of the barrel; and
   means for releasably mechanically coupling the distal end of the plunger to the barrel hub from within the interior of the barrel, said mechanically coupling means including:
      means for rotating the barrel hub about the axis by the plunger so to dismount the barrel hub from the distal end of the barrel, the rotating means including rotary drive surfaces on the distal end of the plunger and the barrel hub, said rotary drive surfaces including axially extending splines formed on the distal end of the plunger and on the barrel hub, the splines mating with each other to provide a positive rotary drive interface; and means for pulling the barrel hub from the distal end of the barrel and to a storage position within the hollow interior of the barrel by the plunger, the pulling means including an axially segmented bulbous plug on one of the distal end of the plunger and the barrel hub and a complementary bulbous pocket on the other of the distal end of the plunger and the barrel hub.

2. The safety syringe of claim 1 further comprising a needle assembly mounted to the barrel hub and extending in a distal direction from the barrel hub, the needle assembly being housed completely within the barrel when the barrel hub is in the storage position.

3. The safety syringe of claim 2 wherein the needle assembly is removably mountable to the barrel hub.

4. The safety syringe of claim 1 wherein the barrel hub and the distal end of the barrel include mating tapered surfaces to provide a fluid seal therebetween.

5. The safety syringe of claim 1 wherein the plunger includes an elongate stem having proximal and distal ends, the piston at the stem distal end.

6. The safety syringe of claim 5 wherein the stem includes a weakened region between the piston and the stem proximal end.

7. The safety syringe of claim 6 wherein the weakened region is adjacent the piston.

8. A safety syringe comprising:
a barrel having proximal and distal ends and a hollow interior defining an axial;
a barrel hub threadably mountable to and dismountable from the distal end of the barrel;
a plunger, having proximal and distal ends, including a piston at the distal end of the plunger, the piston movable within the hollow interior of the barrel, the plunger including an elongate stem with proximal and distal ends and an exterior surface;

means for releasably mechanically coupling the distal end of the plunger to the barrel hub from within the interior of the barrel, said mechanically coupling means including:
means for rotating the barrel hub about the axis by the plunger so to dismount the barrel hub from the distal end of the barrel, the rotating means including axially extending rotary drive spline surfaces on the distal end of the plunger and the barrel hub, said rotary drive spline surfaces being other than surfaces of revolution so to provide a positive rotary drive interface; and
means for pulling the barrel hub from the distal end of the barrel and to a storage position within the hollow interior of the barrel by the plunger, the pulling means including an axially segmented bulbous plug on the barrel hub and a complementary bulbous pocket on the distal end of the plunger;
a needle assembly mounted to the barrel hub and extending in a distal direction from the barrel hub, the needle assembly being housed completely within the barrel when the barrel hub is in the storage position; and
the stem having a step along the exterior surface, the step forming a large diameter portion at the proximal end of the stem, the large diameter portion sized to frictionally engage an inside surface of the distal end of the barrel.

9. The safety syringe of claim 1 wherein the plunger includes an elongate stem with proximal and distal ends and an exterior surface, the stem having a step along the exterior surface, the step forming a large diameter portion at the proximal end of the stem, the large diameter portion sized to frictionally engage an inside surface of the distal end of the barrel.

* * * * *